United States Patent [19]

Whitehurst

[11] 4,404,062

[45] Sep. 13, 1983

[54] CONDENSER

[76] Inventor: Brooks M. Whitehurst, 1983 Hoods Creek Dr., New Bern, N.C. 28560

[21] Appl. No.: 360,646

[22] Filed: Mar. 22, 1982

Related U.S. Application Data

[63] Continuation of Ser. No. 225,400, Jan. 15, 1981, abandoned.

[51] Int. Cl.³ .............................................. B01D 3/02
[52] U.S. Cl. ................................. 202/185 B; 202/186
[58] Field of Search .................... 203/87, 19, DIG. 13; 202/186, 185 B

[56] References Cited

U.S. PATENT DOCUMENTS

| | | | |
|---|---|---|---|
| 2,573,807 | 11/1951 | Piros et al. | 202/186 |
| 3,203,227 | 8/1965 | Donnell | 202/186 |
| 3,687,817 | 8/1972 | Jimerson et al. | 202/185 B |

Primary Examiner—Frank Sever
Attorney, Agent, or Firm—Kenyon & Kenyon

[57] ABSTRACT

The distillation apparatus includes a rectifying column, a reflux condenser and a product condenser. The reflux condenser communicates directly with the interior of the rectifying column in order to return condensed reflux at or near its boiling point. The product condenser is connected to the output of the reflux condenser to condense the product vapors passing from the reflux condenser to obtain a product of high purity.

13 Claims, 4 Drawing Figures

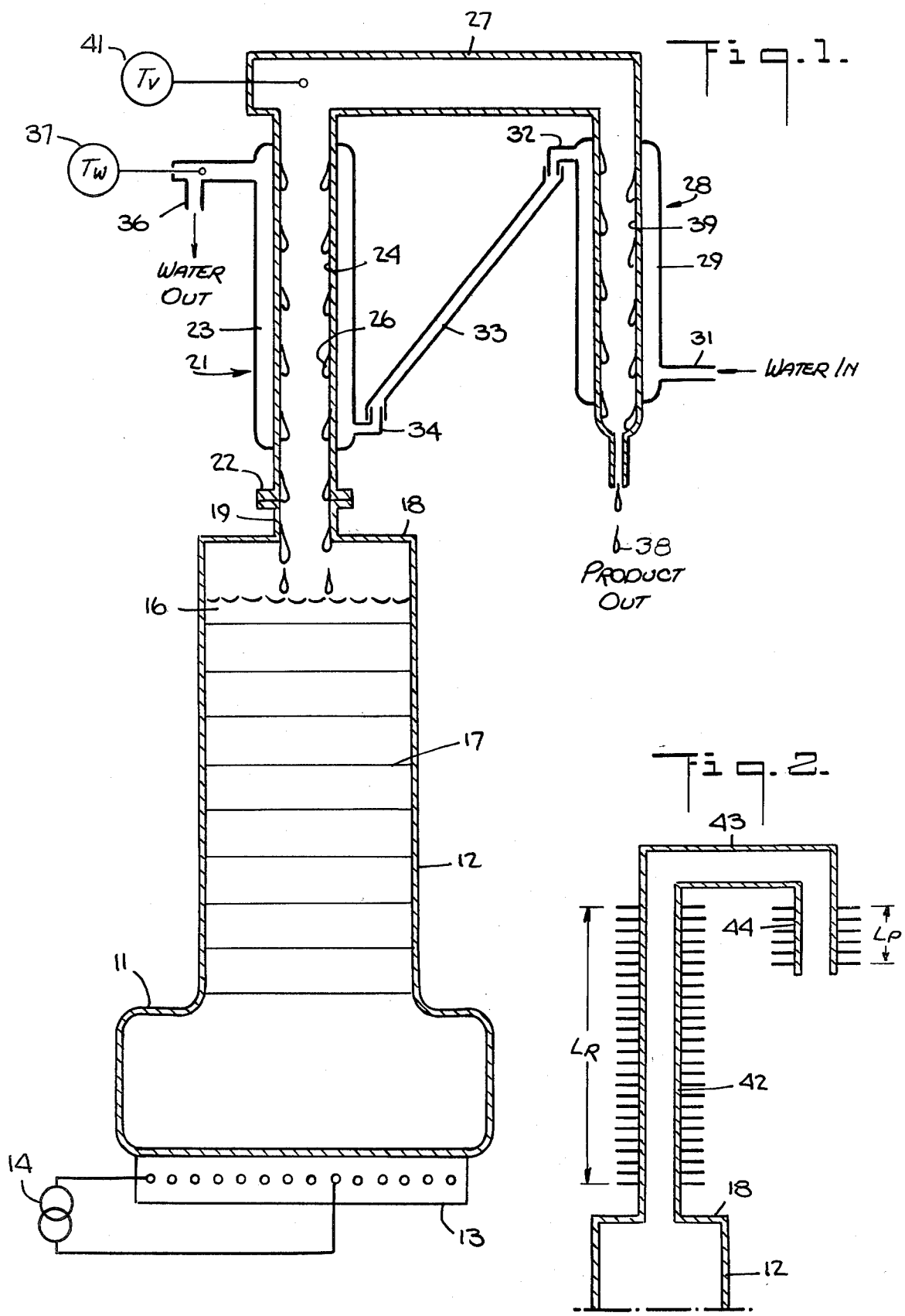

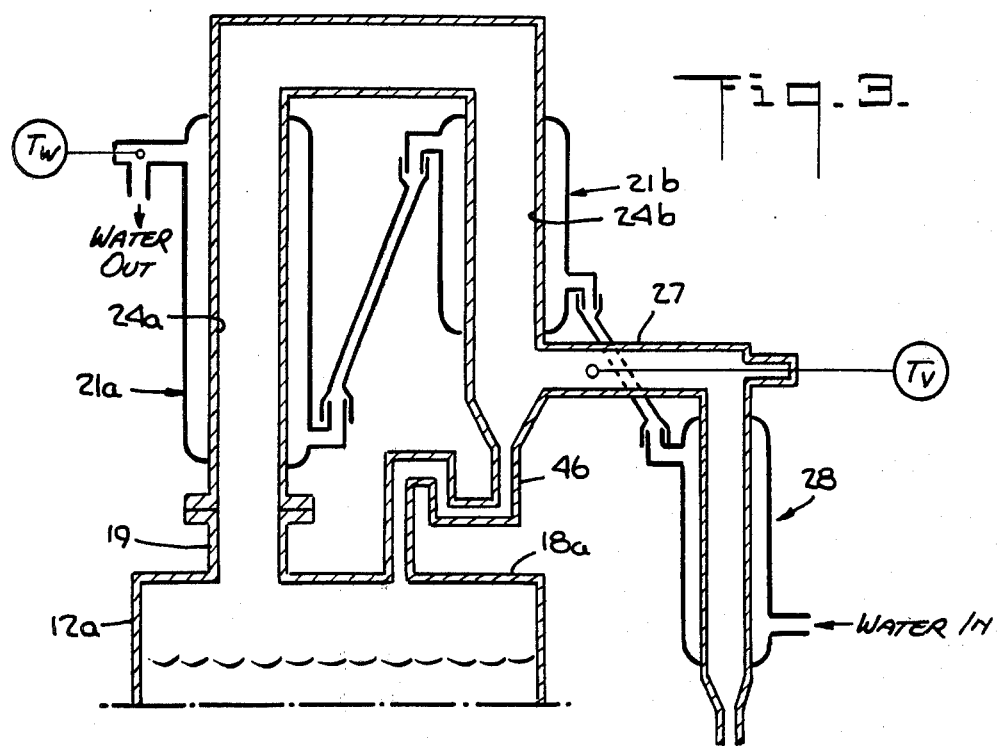
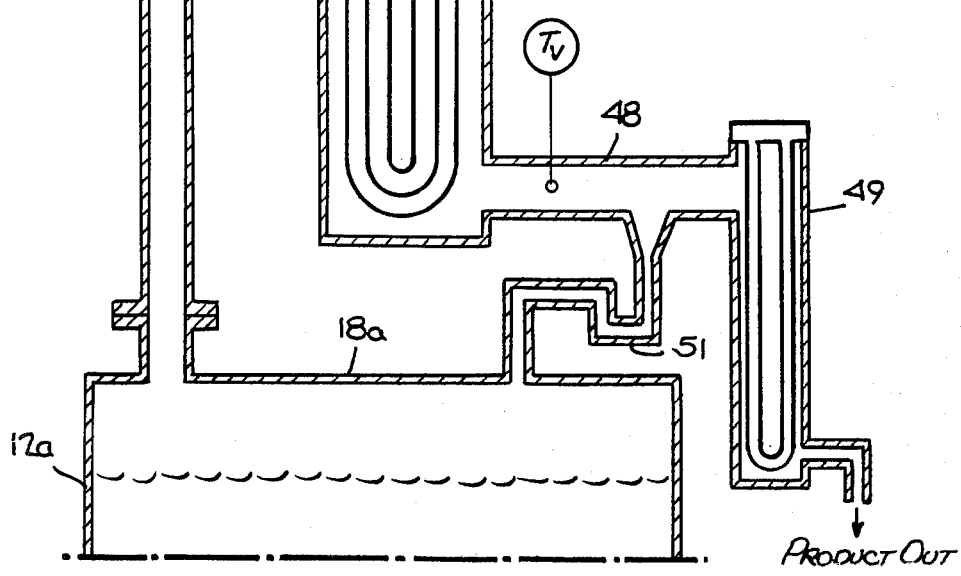

CONDENSER

This is a continuation, of application Ser. No. 225,400 filed Jan. 15, 1981, now abandoned.

BACKGROUND OF THE INVENTION

1. Field of the Invention

This invention relates to the field of distillation condensers including reflux and associated product condensers having condensation surfaces of predetermined related areas to permit efficient separation of liquids having different boiling points. The invention further relates to the method of efficiently separating fluids by successive reflux and product condensation with the refluxed liquid returning directly to a rectifying column on the top of which the reflux condenser is mounted.

2. Prior Art

Distillation apparatus and techniques for separating two liquids of dissimilar boiling points have long been known. Distillation systems to carry out such procedures by utilizing reflux condensers to return to a rectifying column a predetermined percentage of reflux material condensed from vapors emerging from the top of the column, and by causing the vapors emerging from the reflux condenser, to pass through a product condenser are frequently used. The quantities of material handled by such apparatus have been relatively large, justifying the use of relatively complex sensing and control apparatus to make certain that the distillation was efficiently carried out.

However, the shortages of petroleum products that have recently become so burdensome have created a need to find an alternative source of fuel for internal combustion engines. In particular, it is desirable to provide a source of fuel for internal combustion engines on farm equipment, provided the cost of generating such fuel is not excessive.

OBJECTS AND SUMMARY OF THE INVENTION

It is one of the objects of the present invention to provide distillation apparatus suitable for efficiently separating fluids having different boiling points.

Another object of the invention is to provide distillation apparatus that is not only efficient but is simple to use in order to separate fluids having different boiling points.

Another object of the invention is to provide an improved method of operating distillation apparatus to achieve greater efficiency of separation of fluids having different boiling points.

Still another object of the invention is to provide relatively small sized distillation apparatus suitable for use by small enterprises and being sufficiently simple to operate to make it unnecessary to provide elaborate and expensive monitoring and control apparatus.

Further objects will become apparent from the following specification, together with the drawings.

In accordance with the present invention distillation apparatus is provided with means to recondense part of the vapor emerging from the top of a rectifying column and to return the refluxed material directly back into the top of the column while permitting that portion of the vapor that exceeds the condensation capability of the reflux condenser to pass to a product condenser to be recondensed into an output product of high purity. The condensing portion of the distillation apparatus includes a reflux condenser extending upwardly directly from the top of a rectifying column to receive vapor directly from the column and to condense part of that vapor on a condensation surface in the reflux condenser and to allow the refluxed material to flow directly back into the top of the column substantially at the boiling point of the refluxed material. The vapor that passes through the reflux condenser and exceeds the ability of the reflux condenser to recondense it into liquid form flows into a product condenser that extends downwardly from the upper end of the reflux condenser. The product condenser has an upper end that is either connected directly to the upper end of the reflux condenser or is connected thereto by tubular means through which the vapor passes from the reflux condenser to the product condenser.

I have found that it greatly improves the efficiency of distillation apparatus to allow the reflux material to flow directly back into the rectifying column and preferably to do so at a temperature not substantially less than the boiling point of the refluxed material. In addition, I have found that it is desirable that the reflux condenser have a condensation surface with an area larger than the area of the condensation surface of the product condenser and, optimally, approximately three times as large. The size of the condensation surfaces can be determined by the diameters of the product channels through the respective condensers, or they may be determined by the lengths of the respective condensers, or both.

BRIEF DESCRIPTION OF THE DRAWINGS

FIG. 1 is a schematic representation of a still incorporating a condenser system according to the present invention.

FIG. 2 is a schematic representation of an air cooled condenser system according to the invention.

FIG. 3 shows a modified condenser system with a multiple reflux condenser arrangement according to the invention.

FIG. 4 is a schematic representation of a shell and tube heat exchanger condenser system arranged according to the present invention.

DETAILED DESCRIPTION OF THE INVENTION

FIG. 1 shows a distillation system including a still 11 and rectifying column 12 mounted over the still 11 and constructed in accordance with standard practice. A heater 13, which in this instance is an electric heater, is located under the still 11 and is connected to a power supply 14 to provide the necessary heat for the material 16 that is to be distilled. The system is not limited to any particular type of material, but the invention will be described in connection with the application of the apparatus to the separation of ethanol from water. Further in accordance with standard practice, the rectifying column 12 includes packing 17 which may be of any suitable type, such as a plurality of foraminated plates or small solid objects. All of these packing materials and arrangements are well known as are the design and construction of the rectifying column 12 and the still 11.

At the top 18 of the column 12 is a channel 19 through which vapor passes upwardly into a reflux condenser 21 which is mounted on the column 12. The bottom end of the reflux condenser is connected to the upper end of the vapor channel 19 by a flange 22, and in accordance with standard practice, the reflux condenser has a surrounding water jacket 23. Within the reflux condenser is a product channel 24 that is a continuation of the channel 19 and has a surface area of predetermined size on which some of the vapor rising from the column 12 condenses to form droplets 26.

The upper end of the reflux condenser 21 is connected by means of a pipe 27 to the upper end of a product condenser 28. In this embodiment, both of the condensers 21 and 28 have a generally tubular shape and have their axes parallel to each other and to the vertical axis of the column 12.

The product condenser 28 also has a water jacket 29, and the water jackets 23 and 29 are connected together so that water applied to an input nipple 31 at the lower end of the water jacket 29 emerges from an upper nipple 32 and into a pope 33 that connects to a nipple 34 at the lower end of the water jacket 23. Water within the latter water jacket 23 flows upwardly and emerges at an output pipe 36. A thermometer 37 may be inserted in pipe 36 to measure the temperature of the water at this point. The arrangement of water flow in the jackets 23 and 29 is such that the flow in the jacket 29 is counter-current with respect to the flow of recondensed product, while the flow of cooling water in the water jacket 23 is co-current with respect to the flow of vapor in the reflux condenser 21. However, it would be possible to arrange the cooling water connections so that the cooling water flowed in a counter-current direction in the water jacket 23, if desired, and it would also be possible to arrange for the cooling water in the water jacket 29 to flow in the co-current direction.

The vapor that emerges from the top of the reflux condenser 21 and passes through the pipe 27 is condensed in the product condenser 28 and emerges at the lower end of this condenser in the form of a stream or droplets of liquid product 38. The condensation of vapor in the product condenser 28 takes place on the surface of a product channel 39 cooled by the water in the water jacket 29.

In the condenser system in FIG. 1, the two condensers 21 and 28 are approximately equal in length, but the diameter of the product channel 24 in the condenser 21 is larger than the diameter of the product channel 39 in the product condenser 28. In accordance with the present invention it is desirable that the surface area of the condensation surface formed by the wall of the channel 24 be larger than the surface area of the conduction surface formed by the channel 39, and it is preferable that the ratio of these areas be at least 2:1. The optimum size relationship is for the area of the condensation surface of the channel wall 24 to be three times as great as the area of the condensation surface of the channel wall 39. If the ratio is greater than 3:1, the vapor is likely to be constricted, which will diminish the product flow but will not adversely effect the purity of the output product. If the figure is substantially less than 3:1, the purity of the output product will be adversely affected.

A vapor thermometer 41 is shown inserted into the pipe 27 to measure the temperature of the vapor therein. However, it is not necessary to keep track of the temperature of the vapor in order to use this condensing system efficiently. It is important that the reflux 26 be able to return directly to the top 18 of the rectifying column 12 at a temperature as near as possible to the boiling point of the reflux material. In the case of separating ethanol from a mixture of ethanol and water, the temperature of the reflux should be approximately 78.5° C. If the reflux is returned to the column 12 at this temperature, a minimum amount of heat will be required to carry out the distillation. In addition, the amount of vapor passing through the reflux condenser 21 should exceed the capacity of the reflux condenser to condense it out. Thus, the excess of this vapor not condensed in the condenser 21 passes through the pipe 27 to the product condenser 28 where it can be condensed to the liquid product 38.

If the amount of heat supplied by the heater 13 is lower than it should be, less vapor will pass through to the product condenser 28 than that condenser is capable of condensing out. This will diminish the throughput of the system but will not adversely effect the purity of the output product 38. On the other hand, if excessive heat is supplied so that the condenser 28 cannot condense all of the vapor that enters it through the pipe 27, the excess vapor will simply emerge from the lower end of the product condenser still in its vapor state along with the portion of the product that is condensed back to liquid form. This will represent a loss of some of the potentially recoverable product but, again, will not adversely effect the quality of the product that is condensed in the condenser 28. Thus, by proper selection of the relative sizes of the condensation surfaces in the reflux condenser 21 and in the product condenser 28, and by arranging for the reflux to return at the top 18 of the column 12 and at a temperature as nearly as possible at the boiling point of the reflux, this system can be operated without the complex measuring devices and controls that are so common in large distillation systems. Thus, the apparatus shown in FIG. 1 is suitable for operation in small scale distillation, such as the separation of ethanol from a mixture of water and ethanol, and with sufficient purity of the output product to allow it to be used as fuel in an internal combustion engine. It is known that the residual water in ethanol used as such fuel should not exceed about 10%, and the system shown in FIG. 1 has been found to be capable of reducing the residual amount of water in the ethanol output product to about 5%, or less, by volume.

FIG. 2 shows only the condenser system of a modified condenser structure. The arrangement shown in FIG. 2 is especially suitable for a very small still. In FIG. 2, a reflux condenser 42 is formed by using a finned tube, which typically may be copper or stainless steel. The lower end of the reflux condenser 42 is directly connected to the top 18 of the rectifying column 12 to allow reflux to flow directly back into the column. The upper end of the reflux condenser 42 is connected by a pipe 43 to the upper end of a product condenser 44, which is shown as another finned tube.

In the embodiment in FIG. 2, the tubular portions of the reflux condenser 42 and the product condenser 44 may be of the same diameter, and in order to provide the desired ratio of the size of the condensation surfaces in these condensers, the length $L_R$ of the reflux condenser 42 is approximately three times as long as the length $L_P$ of the product condenser 44. Specifically, for a small still that can be heated on a stove or hotplate, the column 12 may be a pipe 1" in diameter and about 28" long filled with aquarium gravel for the packing material and using ¾" copper pipe about 8" long for the reflux condenser 42 and ¾" pipe about 2⅜" long for the product condenser 44. Such a still is capable of producing ethanol at the rate of about one cup per hour and at a purity of about 97% by weight. This is almost at the theoretical limit, since ethanol and water form an azeotrope at about 97.5% ethanol, and the azeotrope cannot be separated by ordinary distillation techniques.

FIG. 3 shows a modified condenser arrangement in which the reflux condenser is divided into two parts, each of which is essentially a complete reflux condenser. One of these parts 21a is connected exactly as the reflux condenser 21 in FIG. 1 and the other part 21b is connected in series with it. In order to allow the reflux formed in the second part 21b to return to the top 18a of the rectifying column 12a, the lowermost end of the reflux condenser part 21b feeds into a trap 46 that empties into the top 18a of the rectifying column 12a.

In this embodiment the output end of the reflux condensers is at the lower portion of the reflux condenser section 21b. This is connected to the pipe 27 that feeds into the product condenser 28, as in FIG. 1.

The embodiment in FIG. 3 has the advantage that the condenser system can be installed in a location where the available height above the top of the column 12a is limited, but it has the disadvantage that the reflux formed in the reflux condenser section 21b is flowing or trickling down the inner wall 24b in the same direction that the vapor is moving toward the product condenser 28. Thus, the reflux and the vapor are moving in a co-current direction in the section 21b rather than in a counter-current direction as is desired and as takes place in the reflux condenser section 21a.

It is still desirable in the embodiment in FIG. 3 to return all reflux material to the top 18a of the column 12a at a temperature as close as possible to the boiling point of that material. This can be achieved by making the trap 46 as short as possible subject to the requirement that it prevent vapor from entering the output end of the reflux condenser.

FIG. 4 shows a modified condenser arrangement using shell and tube heat exchanger condensers. Such condensers are normally used in relatively large distillation apparatus in which they have certain advantages over the simpler types of condensers shown in FIGS. 1-3. In FIG. 4 the same column 12a may be used as in FIG. 3 having an outlet product channel 19 to connect the column 12a to the input side of a shell and tube heat exchanger condenser 47. In such a condenser, the input connection is near the top rather than at the bottom and so the output of this condenser is at the bottom where it connects to a pipe 48 that feeds the vapor to a shell and tube heat exchanger product condenser 49. The pipe 48 also has a take-off connected to a trap 51 that feeds back into the top 18a of the rectifying, or distillation, column 12a. As in all of the other embodiments, the product outlet of the product condenser 49 is at the bottom of that condenser.

Reflux takes place in the condenser 47 and the resulting reflux material is returned to the top 18a of the column 12a at as near as possible the boiling temperature of that material. In addition, the effective condensation surface area of the reflux condenser 47 is preferably about three times the size of the condensation area of the product condenser 49. However, the reflux material flows in a co-current direction with respect to the vapor, and none of the reflux material can return down the entry product channel 19. In these respects, the embodiment shown in FIG. 4 is not as satisfactory as that in FIG. 1, but any loss of efficiency may be more than made up by the efficiency of the shell and tube heat exchanger condensers 47 and 49 over the simpler condensers 21 and 28 in FIG. 1.

The following examples are illustrative of distillation apparatus that has been found to work extremely well in separating ethanol from a mixture of ethanol and water.

EXAMPLE 1

| | |
|---|---|
| Reflux Rate | 1.62 gal./hr. of ethanol |
| Reflux Condenser | ½ inch hard copper, type "M" pipe 17½ inches long, water jacketed |
| Reflux Condenser Surface Area | = 0.191 ft.$^2$ |
| Vapor Velocity at Reflux Condenser Inlet | = 35.5 ft./sec. |
| Product Rate | 0.93 gal./hr. of ethanol |
| Distillation Column, 3 inches Diameter, 5 ft. of Packing, ¼ × ¼ Silica Pebble. | |

The structure used in Example 1 is shown in FIG. 1. It should be noted that the vapor velocity at the reflux condenser inlet is 35.5 feet/second. It is desirable that the velocity not be too high, and in fact, not substantially higher than about 35 or 40 feet/second so as not to entrain drops of the reflux material and carry them over into the product condenser.

When this structure was tested, it produced ethanol at a production rate of about 0.93 gal./hr., and the purity of the ethanol was 93%. This was based on an initial mixture of water and ethanol in the still 11 in which the still bottom concentration of ethanol was 4%. It can be seen that this represents a very high efficiency of separation of the ethanol and water to go from 4% to 93%.

Example 2 used the structure shown in FIG. 3 with each of the reflux condenser sections 21a and 21b being about 22" long, making a total reflux condenser of 44" length.

EXAMPLE 2

| | |
|---|---|
| Reflux Rate | 8.75 gal./hr. of ethanol |
| Reflux Condenser | 1 inch hard copper, type "M" pipe 44 inches long, water jacketed |
| Reflux Condenser Surface Area | = 1.033 ft.$^2$ |
| Vapor Velocity at Reflux Condenser Inlet | = 47.9 ft./sec. |
| Product Rate | 5 gal./hr. of ethanol |
| Product Condenser | 0.59 ft.$^2$, 3 ft. of ¾ hard copper type "M" pipe, water jacketed |
| Vapor Velocity at Product Condenser Inlet | = 30.9 ft./sec. |
| Distillation Column, 6 inches Diameter, 12 ft. of Packing, ½ inch Porcelain, Intalox Saddles. | |

The following values were observed in testing this apparatus:

| | |
|---|---|
| Production Rate | 8 gal./hr. |
| Product Quality | 95% ethanol |
| Still Bottom Concentration | 8% ethanol |

Example 3 used the structure shown in FIG. 1.

EXAMPLE 3

| | |
|---|---|
| Reflux Rate | 6 gal./hr. ethanol |
| Reflux Condenser | 1 inch hard copper, type "M" pipe 32 inches long, water jacketed |
| Reflux Condenser Surface Area | = 0.71 ft.$^2$ |
| Vapor Velocity at Reflux Condenser Inlet | = 25.8 ft./sec. |
| Product Rate | 1.5 gal./hr. ethanol |
| Product Condenser | 0.177 ft.$^2$ required, actually constructed to contain 0.354 ft.$^2$, 32 inches of ½ hard copper, type "M" pipe, water jacketed |
| Vapor Velocity at Product Condenser Inlet based on | |

| | |
|---|---|
| 1.5 gal./hr. of product | 20.7 ft./sec. |
| Distillation Column | 4 inches Diameter, 6 ft. of Packing, ⅜ inch Porcelain Intalox Saddles. |

The following tests were carried out using the apparatus in this example to show the effect of operating the apparatus at different production rates:

| Test 3A | |
|---|---|
| Production Rate | 3.96 gal./hr. |
| Product Quality | 95% ethanol |
| Still Bottom Concentration = 33% ethanol | |
| Reflux Condenser Cooling Water Temperature ($T_W$) 130° to 120° F. | |
| Vapor Temperature ($T_V$) 173° F. | |

| Test 3B | |
|---|---|
| Production Rate | 1.52 gal./hr. |
| Product Quality | 96% ethanol |
| Still Bottom Concentration = 33% ethanol | |
| Reflux Condenser Cooling Water Temperature ($T_2$) 110° to 120° F. | |
| Vapor Temperature ($T_V$) 173° F. | |

| Test 3C | |
|---|---|
| Production Rate | 2.23 gal./hr. |
| Product Quality | 95% ethanol |
| Still Bottom Concentration = 33% ethanol | |
| Reflux Condenser Cooling Water Temperature ($T_W$) 110° to 120° F. | |
| Vapor Temperature ($T_V$) 173° F. | |

As may be seen in all of the examples, the quality of the ethanol was within the range suitable for use as a fuel for internal combustion engines.

What is claimed is:

1. A distillation apparatus comprising elements arranged, sized and dimensioned to provide a product condensate with a purity of at least 95% from a feed of ethanol and water, said elements including:
    a still;
    a rectifying column mounted over said still;
    a reflux condenser mounted over said column to receive a flow of vapor therefrom, said condenser having a first product channel with a surface area for condensing at least some of the vapor thereon to form reflux, said product channel opening directly into said column at a lower end to deliver the reflux directly to said column; and
    a product condenser in communication with said reflux condenser to receive the remainder of the vapor therefrom, said product condenser having a second product channel with a surface area for condensing the received vapor thereon to form a product, said surface area of said second product channel being smaller than said surface area of said first product channel.

2. The apparatus of claim 1 in which the area of the condensation surface of said reflux condenser is greater than twice the area of the condensation surface of the product condenser.

3. The apparatus of claim 1 in which said rectifying column is a vertical column, and said reflux condenser is generally cylindrical and extends substantially vertically directly from the top of said rectifying column and the vapor output end of said reflux condenser is at the upper end thereof.

4. The apparatus of claim 3 in which said product condenser is generally cylindrical and extends downwardly substantially parallel to said reflux condenser.

5. The apparatus of claim 1 in which said first product channel is substantially straight and extends straight from the top of said rectifying column and has a substantially uniform cross-sectional area, and said second product channel is straight and has a substantially uniform cross-sectional area, the length of said first product channel being substantially equal to the length of said second product channel and the inner surface of said first product channel of the reflux condenser being greater than twice as large as the inner surface of said second product channel of said product condenser.

6. The apparatus of claim 1 in which said product condenser is approximately one-third as long as said reflux condenser.

7. The apparatus of claim 1 in which said reflux condenser comprises a first heat conductive metal pipe, and said product condenser comprises a second heat conductive metal pipe, the apparatus further comprising:
    first air-cooling fin means surrounding said reflux condenser and extending longitudinally along said reflux condenser; and
    second air-cooling fin means surrounding said product condenser and extending along the outer surface thereof.

8. A distillation apparatus as set forth in claim 1 wherein said surface area of said first product channel is three times said surface area of said second product channel.

9. A distillation apparatus as set forth in claim 1 which further comprises a pipe connecting an upper end of said reflux condensor to an upper end of said product condenser.

10. A distillation apparatus as set forth in claim 1 wherein said reflux condenser includes two parts connected in series, one of said parts defining said first product channel and the other of said parts having a product channel and a trap at a lower end connected to said rectifying column.

11. A distillation apparatus as set forth in claim 1 which further comprises a shell and tube heat exchanger condenser between said reflux condenser and said product condenser, a pipe between said heat exchanger condenser and said product condenser and a trap between said pipe and said column.

12. In a distillation system having elements arranged, sized and dimensioned to provide a product condensate with a purity of at least 95% from a feed of ethanol and water, the combination of
    a reflux condenser having a vertically disposed product channel with a surface area for condensing a part of a rising vapor thereon to form a reflux, said channel having an open lower end to direct reflux therefrom; and
    a product condenser in communication with said reflux condenser to receive the remaining part of the vapor therefrom, said product condenser having a second product channel with a surface area for condensing the received vapor thereon to form a product and a product outlet at a bottom thereof, said surface area of said second product channel being smaller than said surface area of said product channel of said reflux condenser.

13. The combination as set forth in claim 12 wherein said surface areas of said product channels are in a ratio of 3:1.

* * * * *